United States Patent
Tamura et al.

(10) Patent No.: US 10,364,223 B2
(45) Date of Patent: Jul. 30, 2019

(54) ORGANIC COMPOUND, ELECTROCHROMIC ELEMENT, OPTICAL FILTER, LENS UNIT, IMAGE PICKUP APPARATUS, AND WINDOW MEMBER

(71) Applicant: CANON KABUSHIKI KAISHA, Tokyo (JP)

(72) Inventors: Tetsuya Tamura, Kawasaki (JP); Satoshi Igawa, Fujisawa (JP)

(73) Assignee: CANON KABUSHIKI KAISHA, Tokyo (JP)

(*) Notice: Subject to any disclaimer, the term of this patent is extended or adjusted under 35 U.S.C. 154(b) by 5 days.

(21) Appl. No.: 15/895,056

(22) Filed: Feb. 13, 2018

(65) Prior Publication Data

US 2018/0237393 A1     Aug. 23, 2018

(30) Foreign Application Priority Data

Feb. 20, 2017 (JP) .................. 2017-028821

(51) Int. Cl.
  *C09K 9/02* (2006.01)
  *G09G 3/38* (2006.01)
  (Continued)

(52) U.S. Cl.
  CPC .......... *C07D 213/06* (2013.01); *C07C 317/04* (2013.01); *C07D 213/22* (2013.01);
  (Continued)

(58) Field of Classification Search
  CPC .......... G02F 1/15; G02F 1/1503; G02F 1/153; G02F 1/155; G02F 1/157; G02F 1/161;
  (Continued)

(56) References Cited

U.S. PATENT DOCUMENTS

| 7,582,363 B2 * | 9/2009 | Takahashi | C07F 9/5045 252/301.18 |
| 8,044,224 B2 * | 10/2011 | Carreira | C07B 53/00 556/137 |

(Continued)

FOREIGN PATENT DOCUMENTS

| JP | 2013-193991 A | 9/2013 |
| JP | 2015-124228 A | 7/2015 |

*Primary Examiner* — Loha Ben
(74) *Attorney, Agent, or Firm* — Venable LLP

(57) ABSTRACT

Provided is an organic compound, which is represented by the general formula (1):

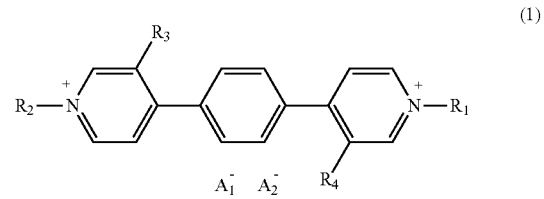

in the general formula (1), $R_1$ and $R_2$ are each independently selected from the group consisting of an alkyl group having 1 or more and 20 or less carbon atoms, an aryl group, an aralkyl group, and a heteroaryl group, $R_3$ and $R_4$ are each independently selected from an alkyl group having 1 or more and 10 or less carbon atoms, and an alkoxy group having 1 or more and 10 or less carbon atoms, and $A_1^-$ and $A_2^-$ each independently represent a monovalent anion.

15 Claims, 4 Drawing Sheets

(51) Int. Cl.
  *G02F 1/153* (2006.01)
  *G02F 1/155* (2006.01)
  *C07C 317/04* (2006.01)
  *C07D 213/06* (2006.01)
  *C07D 213/22* (2006.01)
  *C07D 401/14* (2006.01)
  *C07F 9/6558* (2006.01)
  *G02F 1/1503* (2019.01)

(52) U.S. Cl.
  CPC .............. *C07D 401/14* (2013.01); *C09K 9/02* (2013.01); *G02F 1/1503* (2019.01); *G02F 1/155* (2013.01); *G09G 3/38* (2013.01); *C07F 9/65586* (2013.01); *C09K 2211/1018* (2013.01); *C09K 2211/1022* (2013.01); *C09K 2211/1044* (2013.01); *G02F 1/153* (2013.01); *G02F 2202/02* (2013.01)

(58) Field of Classification Search
  CPC .............. G02F 1/163; G02F 2001/1502; G02F 2202/02; C07D 211/98; C07D 213/06; C07D 213/127; C07D 213/22; C07D 213/65; C07D 317/60; C07D 401/14; C07D 409/14; C07C 317/04; C07C 317/14; C07C 317/16; C07C 317/26; C07F 9/6553; C07F 9/6558; C07F 9/65583; C07F 9/65586; C09K 9/02; C09K 11/06; C09K 2211/1014; C09K 2211/1018; C09K 2211/1022; C09K 2211/1044; G09G 3/34; G09G 3/38
  USPC ................ 359/265, 266, 275; 428/913, 917; 252/301.18, 301.19, 582, 583, 585–589; 345/105; 540/571, 576, 581
  See application file for complete search history.

(56) References Cited

U.S. PATENT DOCUMENTS

| | | | |
|---|---|---|---|
| 8,507,669 B2* | 8/2013 | Kubota | ............... C07D 317/60 540/543 |
| 9,766,527 B2 | 9/2017 | Kubo et al. | |
| 9,869,919 B2 | 1/2018 | Kubo et al. | |
| 9,954,187 B2* | 4/2018 | Takahashi | ........... H01L 51/0058 |
| 2017/0329195 A1* | 11/2017 | Igawa | ................. C07F 9/65583 |
| 2018/0044581 A1* | 2/2018 | Sagisaka | ................ G02F 1/155 |
| 2018/0052375 A1 | 2/2018 | Yamada et al. | |
| 2018/0259849 A1* | 9/2018 | Hirai | ...................... H01L 27/14 |

* cited by examiner

ORGANIC COMPOUND, ELECTROCHROMIC ELEMENT, OPTICAL FILTER, LENS UNIT, IMAGE PICKUP APPARATUS, AND WINDOW MEMBER

BACKGROUND OF THE INVENTION

Field of the Invention

The present disclosure relates to an organic compound, and an electrochromic element, an optical filter, a lens unit, an image pickup apparatus, and a window member each including the compound.

Description of the Related Art

Various materials have been reported as electrochromic (hereinafter sometimes abbreviated as "EC") materials whose optical absorption properties (a colored state and a light transmittance) are changed by the electrochemical redox reactions of the substances. Conductive polymers, such as polythiophene and polyaniline, and organic low-molecular weight compounds, such as oligothiophene, have been known as organic EC materials.

Examples of the organic low-molecular weight compounds serving as the organic EC materials include a viologen derivative that is a cathodic compound colored by its reduction and a phenazine derivative that is an anodic compound colored by its oxidation. Each of those organic low-molecular weight compounds serving as the organic EC materials transmits visible light in a neutral state because the compounds have n-conjugation lengths shorter than those of the conductive polymers and hence each have absorption in an ultraviolet region. In addition, the anodic compound absorbs visible light in an oxidized state, and the cathodic compound absorbs visible light in a reduced state. This is because the conjugation length of the oxidized state or the reduced state is longer than the conjugation length of the neutral state, and hence a wavelength region in which light is absorbed becomes a visible light region. In other words, each of the organic low-molecular weight compounds serving as the organic EC materials is bleached in the neutral state, and is colored in the oxidized state or the reduced state. Many compounds have been proposed as both the cathodic compound and the anodic compound, and their applications cover a broad spectrum.

A typical cathodic compound is, for example, a 4,4'-bipyridinium compound (viologen). In Japanese Patent Application Laid-Open No. 2015-124228, as a method of lengthening the absorption wavelength of the viologen at the time of its coloring, there is a description of a method involving introducing an aromatic ring into a space between the two pyridine structures of 4,4'-bipyridine. In Japanese Patent Application Laid-Open No. 2013-193991, there is a description of a method involving introducing a heterocycle into the space between the two pyridine structures of 4,4'-bipyridine.

Compounds each having a tricyclic structure obtained by introducing an aromatic ring or a heterocycle into the space between the two pyridine rings of 4,4'-bipyridine described in Japanese Patent Application Laid-Open No. 2015-124228 and Japanese Patent Application Laid-Open No. 2013-193991 each show a local maximum absorption wavelength around 500 nm in a reduced state, and hence the absorption wavelength is lengthened as compared to the absorption wavelength of the viologen.

SUMMARY OF THE INVENTION

An object of the present disclosure is to provide an organic compound that shows coloring absorption at a wavelength longer than those of the related-art compounds each having a tricyclic structure in a reduced state while securing its transparency at the time of bleaching.

An organic compound of the present disclosure is represented by the following general formula (1):

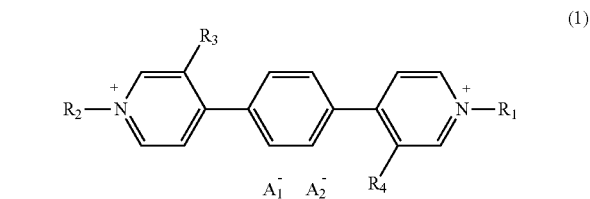

in the general formula (1), $R_1$ and $R_2$ are each independently selected from the group consisting of an alkyl group having 1 or more and 20 or less carbon atoms, an aryl group, an aralkyl group, and a heteroaryl group, and the alkyl group, the aryl group, the aralkyl group, and the heteroaryl group may each have a substituent, $R_3$ and $R_4$ are each independently selected from the group consisting of an alkyl group having 1 or more and 10 or less carbon atoms, and an alkoxy group having 1 or more and 10 or less carbon atoms, and $A_1^-$ and $A_2^-$ each independently represent a monovalent anion.

Further features of the present invention will become apparent from the following description of exemplary embodiments with reference to the attached drawings.

DESCRIPTION OF THE EMBODIMENTS

Figure 1:
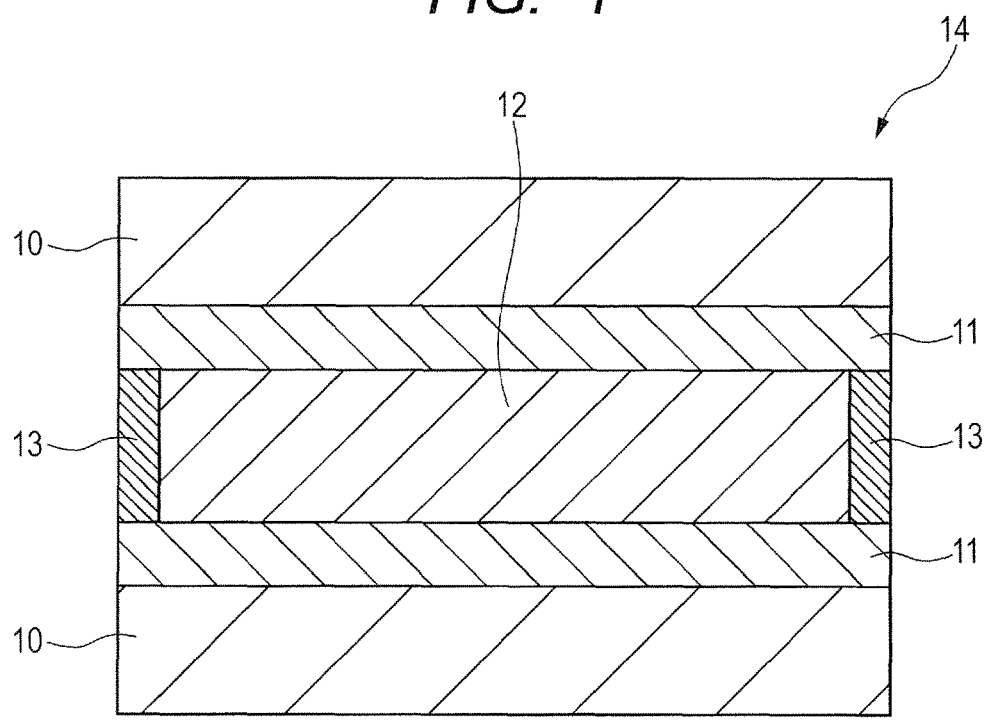
FIG. 1 is a schematic sectional view of an example of an electrochromic element of the present invention.

Preferred embodiments of the present invention will now be described in detail in accordance with the accompanying drawings.

<Organic Compound>

An organic compound of the present disclosure is an organic compound having an electrochromic property (EC property). The EC property refers to the following property: an electrochemical redox reaction reversibly progresses to change the optical absorption properties (colored state and light transmittance) of a substance, and hence its color tone changes. The term "colored" as used herein means that a transmittance at a specific wavelength reduces. In the following description, an organic compound having an EC property is sometimes referred to as "electrochromic compound (EC compound)."

An organic compound according to the present disclosure is represented by the following general formula (1):

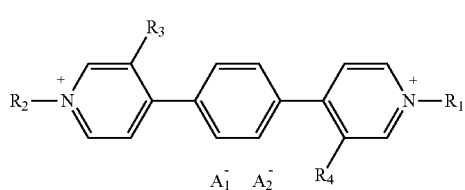

(1)

in the general formula (1), $R_1$ and $R_2$ are each independently selected from the group consisting of an alkyl group having 1 or more and 20 or less carbon atoms, an aryl group, an aralkyl group, and a heteroaryl group, and the alkyl group, the aryl group, the aralkyl group, and the heteroaryl group may each have a substituent, $R_3$ and $R_4$ are each independently selected from the group consisting of an alkyl group having 1 or more and 10 or less carbon atoms, and an alkoxy group having 1 or more and 10 or less carbon atoms, and $A_1^-$ and $A_2^-$ each independently represent a monovalent anion.

The organic compound represented by the general formula (1) is specifically described below. However, the present invention is not limited thereto.

The alkyl group having 1 or more and 20 or less carbon atoms, the alkyl group serving as a group represented by any one of $R_1$ and $R_2$, may be linear, branched, or cyclic. A hydrogen atom of the alkyl group may be substituted with a fluorine atom or an ester group, and a methyl group in the alkyl group may be substituted with a cyano group. Examples of the alkyl group having 1 or more and 20 or less carbon atoms, the alkyl group serving as a group represented by any one of $R_1$ and $R_2$, include a methyl group, an ethyl group, a n-propyl group, an isopropyl group, a n-butyl group, a t-butyl group, an octyl group, a cyclohexyl group, and a trifluoromethyl group.

Examples of the aryl group serving as a group represented by any one of $R_1$ and $R_2$ include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

Examples of the aralkyl group serving as a group represented by any one of $R_1$ and $R_2$ include a benzyl group and a phenethyl group.

Examples of the heteroaryl group serving as a group represented by any one of $R_1$ and $R_2$ include a pyridyl group, a pyrazyl group, and a pyrimidyl group.

The groups represented by $R_1$ and $R_2$ may each have an adsorbing group for adsorbing to a porous electrode at a terminal thereof. Specific examples of the adsorbing group include a carboxyl group, a sulfonic acid group, a phosphonic acid group, a phosphate group, and a trialkoxysilyl group.

Examples of the substituents that the groups represented by $R_1$ and $R_2$ may have include: halogen atoms, such as fluorine, chlorine, bromine, and iodine; alkyl groups, such as a methyl group, an ethyl group, a propyl group, an isopropyl group, a t-butyl group, and a cyclohexyl group, and groups obtained by substituting hydrogen atoms of the alkyl groups with fluorine atoms; alkoxyl groups, such as a methoxyl group, an ethoxyl group, and a propoxyl group; aryl groups, such as a phenyl group and a biphenyl group; aralkyl groups, such as a benzyl group and a phenethyl group; heteroaryl groups, such as a thienyl group, a pyrrolyl group, and a pyridyl group; substituted amino groups, such as a dimethylamino group, a diethylamino group, a dibenzylamino group, a diphenylamino group, a ditolylamino group, and a dianisolylamino group; aryloxyl groups, such as a phenoxyl group; acyl groups, such as an acetyl group and a benzoyl group; carboxylic acid alkyl ester groups, such as a carboxylic acid methyl ester group and a carboxylic acid ethyl ester group; and a cyano group. Of those, a halogen atom, an alkyl group having 1 or more and 4 or less carbon atoms, an alkoxy group having 1 or more and 4 or less carbon atoms, an aryl group, an aralkyl group, or a heteroaryl group is preferred. In addition, the groups represented by $R_1$ and $R_2$ are each preferably an aryl group, aralkyl group, or heteroaryl group having any such substituent.

The monovalent anions represented by $A_1^-$ and $A_2^-$ are each selected from, for example, $PF_6^-$, $ClO_4^-$, $BF_4^-$, $AsF_6^-$, $SbF_6^-$, $CF_3SO_3^-$, $(CF_3SO_2)_2N^-$, and halide ions, such as $Br^-$, $Cl^-$, and $I^-$. Of those, $PF_6^-$, $BF_4^-$, $CF_3SO_3^-$, or $(CF_3SO_2)_2N^-$ is preferred. In addition, $A_1^-$ and $A_2^-$, which may be different anions or may be the same anion, are preferably the same anion.

The alkyl group having 1 or more and 10 or less carbon atoms, the alkyl group serving as a group represented by any one of $R_3$ and $R_4$, may be linear, branched, or cyclic. Although the alkyl group having 1 or more and 10 or less carbon atoms, the alkyl group serving as a group represented by any one of $R_3$ and $R_4$, is preferably unsubstituted, a hydrogen atom of the alkyl group may be substituted with a fluorine atom or an ester group, and a methyl group in the alkyl group may be substituted with a cyano group. Examples of the alkyl group having 1 or more and 10 or less carbon atoms, the alkyl group serving as a group represented by any one of $R_3$ and $R_4$, include a methyl group, an ethyl group, a n-propyl group, an isopropyl group, a n-butyl group, a t-butyl group, an octyl group, a cyclohexyl group, and a trifluoromethyl group. The number of carbon atoms of the alkyl group is preferably 1 or more and 8 or less, more preferably 1 or more and 4 or less.

The alkoxy group having 1 or more and 10 or less carbon atoms represented by any one of $R_3$ and $R_4$ may be linear, branched, or cyclic. Although the alkoxy group having 1 or more and 10 or less carbon atoms, the alkyl group serving as a group represented by any one of $R_3$ and $R_4$, is preferably unsubstituted, a hydrogen atom of the alkoxy group may be substituted with a fluorine atom. Examples of the alkoxy group having 1 or more and 10 or less carbon atoms, the alkoxy group serving as a group represented by any one of $R_3$ and $R_4$, include a methoxy group, an ethoxy group, an isopropyloxy group, a t-butyloxy group, an octyloxy group, a cyclohexyloxy group, and a trifluoromethyloxy group. The number of carbon atoms of the alkoxy group is preferably 1 or more and 8 or less, more preferably 1 or more and 4 or less.

Although a method of producing the compound of the present invention is not particularly limited, the compound may be produced by, for example, the following method. Description is given by taking a case in which $R_3$ and $R_4$ each represent a methyl group as an example.

When $R_1$ and $R_2$ each represent an alkyl group or an aralkyl group, first, an organic compound represented by the following general formula (2) (Intermediate 1) and a compound having a halogenated alkyl group or a halogenated alkoxy group, or having a halogen in the alkyl moiety of an aralkyl group are caused to react with each other in a predetermined solvent to provide a salt derived from Intermediate 1. Here, the solvent is preferably a polar solvent, such as acetonitrile or N,N-dimethylformamide, though the solvent is not particularly limited. After that, the resultant salt derived from Intermediate 1 and a salt containing a desired anion are subjected to an anion exchange reaction in a predetermined solvent. Thus, the compound of the present invention can be produced. Here, a solvent that can dissolve both the salt derived from Intermediate 1 and the salt containing the desired anion is preferably used as the solvent to be used in the anion exchange reaction.

When $R_1$ and $R_2$ each represent an aryl group, Intermediate 1 and a 2,4-dinitrophenyl halide are caused to react with each other, and then the resultant is caused to react with a desired arylamine. After that, the resultant and the salt containing the desired anion are subjected to an anion exchange reaction in the predetermined solvent. Thus, the compound of the present invention can be produced.

When $R_1$ and $R_2$ each represent a heteroaryl group, Intermediate 1 and a halogenated heteroaryl compound are caused to react with each other in the solvent to provide a salt derived from Intermediate 1. After that, the resultant salt derived from Intermediate 1 and the salt containing the desired anion are subjected to an anion exchange reaction in the predetermined solvent. Thus, the compound of the present invention can be produced.

With regard to the introduction of $R_1$ and $R_2$ into nitrogen atoms, only one of the two nitrogen atoms of Intermediate 1 may be subjected to a reaction by selecting, for example, the amount of a compound to be used, a solvent, and a reaction temperature. When $R_1$ and $R_2$ are introduced onto the two nitrogen atoms of Intermediate 1 in a stepwise manner, $R_1$ and $R_2$ identical to each other may be introduced into the two nitrogen atoms of Intermediate 1, or $R_1$ and $R_2$ different from each other may be introduced thereinto.

(2)

Although a method of producing Intermediate 1 is not particularly limited, the intermediate may be synthesized by, for example, a coupling reaction between 1,4-phenylenediboronic acid and 4-chloro-3-methylpyridine as shown below.

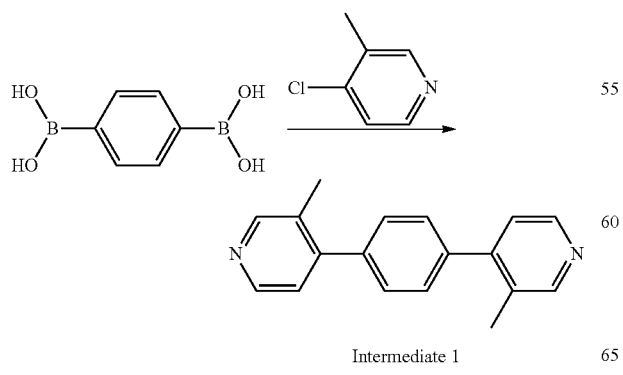

Intermediate 1

Specific structural formulae of the organic compound represented by the general formula (1) are listed below. However, the organic compound represented by the general formula (1) according to the present disclosure is not limited thereto.

A-1
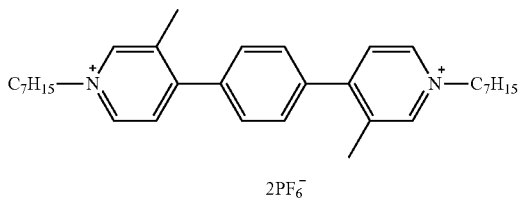
$2PF_6^-$

A-2
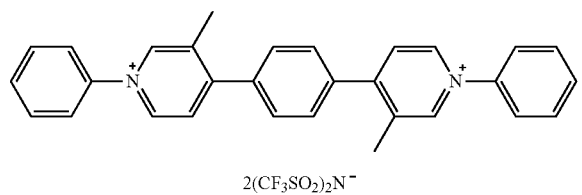
$2(CF_3SO_2)_2N^-$

A-3
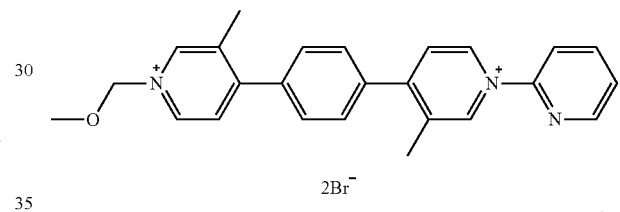
$2Br^-$

A-4
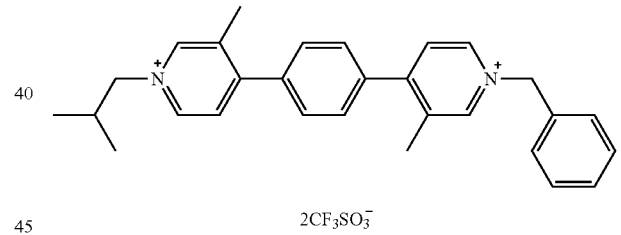
$2CF_3SO_3^-$

A-5
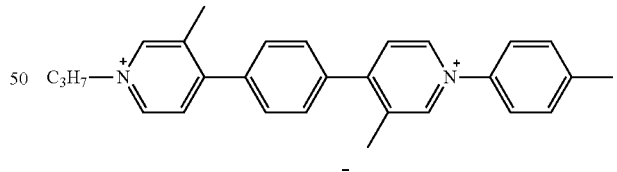
$2Br^-$

A-6
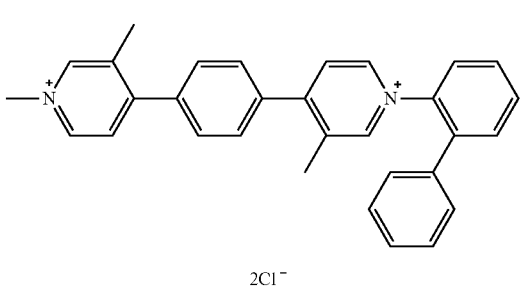
$2Cl^-$

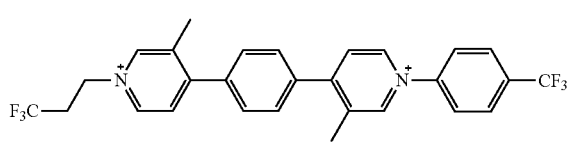

-continued

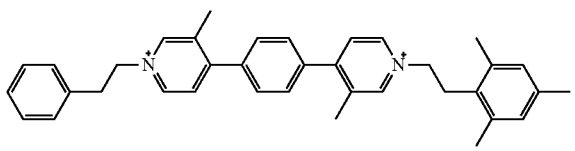

A-18

2BF$_4^-$

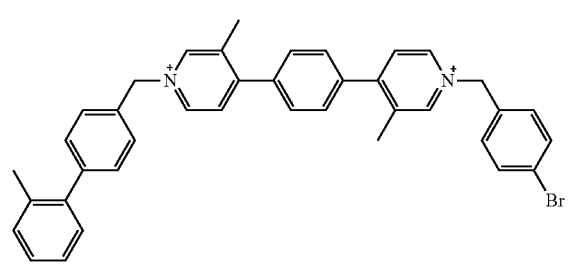

A-19

Br$^-$ Cl$^-$

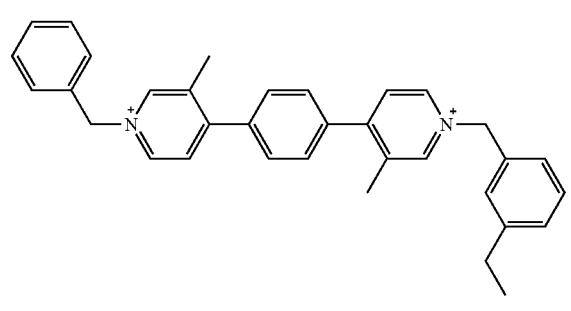

A-20

Br$^-$ I$^-$

The organic compound of the present invention has a structure represented by the general formula (1), and a molecule thereof has a twisted structure in a neutral state as a result of the introduction of $R_3$ and $R_4$. Accordingly, even when the organic compound of the present invention is dissolved in a solvent, the solution of the organic compound of the present invention has high transparency. In addition, the organic compound of the present invention is such an EC compound that an electrochemical redox reaction reversibly progresses to make its optical absorption properties (colored state and light transmittance) in a reduced state and those in the neutral state different from each other. That is, the organic compound of the present invention is a cathodic EC compound that is colored in the reduced state. The organic compound of the present invention has a local maximum absorption wavelength in the range of 570 nm or more, preferably from 570 nm or more to 800 nm or less in the reduced state (colored state). As can be seen from the foregoing, the organic compound of the present invention is a compound having a local maximum absorption wavelength longer than the local maximum absorption wavelengths of the related-art compounds each having a tricyclic structure described in Japanese Patent Application Laid-Open No. 2015-124228 and Japanese Patent Application Laid-Open No. 2013-193991.

<Electrochromic Element (EC Element)>

An electrochromic element (EC element) of the present invention includes a pair of electrodes and an electrochromic layer (EC layer) arranged between the pair of electrodes, and the EC layer contains the organic compound of the present invention. The EC element of the present invention is described below with reference to the drawings.

An EC element 14 of FIG. 1 is the EC element 14 including a pair of transparent electrodes 11 and an EC layer 12 arranged between the pair of electrodes 11. The inter-electrode distance of the pair of electrodes 11 is kept constant by spacers 13. In the EC element 14, the pair of electrodes 11 is arranged between a pair of transparent substrates 10. The EC layer 12 contains the organic compound of the present invention and an electrolyte. The EC layer 12 may have: a layer formed of an EC compound that is the organic compound of the present invention; and a layer formed of the electrolyte. In addition, the EC layer 12 may be arranged as a solution containing the EC compound that is the organic compound of the present invention and the electrolyte. The EC element 14 of the present invention is preferably the EC element 14 in which the EC layer 12 is a solution. The constituents of the EC element 14 are described below.

(EC Layer 12)

When the electrolyte is an ion dissociative salt, the electrolyte is not limited as long as the electrolyte is a compound having satisfactory solubility in a solvent. In addition, when the electrolyte is a solid electrolyte, the electrolyte is not limited as long as the electrolyte is a compound showing high compatibility with the compound of the present invention. Of such electrolytes, an electrolyte having an electron-donating ability is preferred. Those electrolytes may also be referred to as "supporting electrolytes." Examples of the electrolyte include various inorganic ion salts, such as alkali metal salts and alkaline earth metal salts, quaternary ammonium salts, and cyclic quaternary ammonium salts. Specific examples thereof include: alkali metal salts of Li, Na, and K, such as $LiClO_4$, $LiBF_4$, $LiAsF_6$, $LiCF_3SO_3$, $LiPF_6$, LiI, NaI, $NaClO_4$, $NaBF_4$, $NaAsF_6$, and KCl; and quaternary ammonium salts, such as $(CH_3)_4NBF_4$, $(C_2H_5)_4NBF_4$, $(n-C_4H_9)_4NBF_4$, $(n-C_4H_9)_4NPF_6$, $(C_2H_5)_4NBr$, $(C_2H_5)_4NClO_4$, and $(n-C_4H_9)_4NClO_4$, and cyclic quaternary ammonium salts.

Although a solvent that dissolves the organic compound of the present invention and the electrolyte is not particularly limited as long as the solvent can dissolve the compound and the electrolyte, a solvent having polarity is particularly preferred. Specific examples thereof include water and organic polar solvents, such as methanol, ethanol, propylene carbonate, ethylene carbonate, dimethyl sulfoxide, dimethoxyethane, γ-butyrolactone, γ-valerolactone, sulfolane, dimethylformamide, dimethoxyethane, tetrahydrofuran, acetonitrile, propionitrile, benzonitrile, dimethylacetamide, methylpyrrolidinone, and dioxolane.

The EC layer 12 may further contain a polymer or a gelling agent to make the EC layer 12 a highly viscous one or a gel-like one before use. The polymer is not particularly limited, and examples thereof include polyacrylonitrile, carboxymethylcellulose, polyvinyl chloride, polyethylene oxide, polypropylene oxide, polyurethane, polyacrylate, polymethacrylate, polyamide, polyacrylamide, polyester, and Nafion (trademark).

The EC element of the present invention may contain the organic compound of the present invention and another kind of organic compound different from the organic compound of the present invention. The number of kinds of the other kind of organic compounds may be one kind or two or more kinds. The other kind of organic compound may be a compound that is colored in an oxidized state, may be a compound that is colored in a reduced state, or may be both of the compounds. The other kind of organic compound may not be an EC compound. In particular, a compound that is colored in an oxidized state is preferably incorporated. The term "compound that is colored in an oxidized state" refers to such a compound that its visible light transmittance in the oxidized state is lower than its visible light transmittance in a reduced state.

The organic compound of the present invention can serve as an EC element to develop a desired color when combined with a coloring material of any other color. The absorption wavelength region of the coloring material of any other color at the time of its coloring falls within the range of preferably from 400 nm or more to 800 nm or less, more preferably from 420 nm or more to 700 nm or less. When the organic compound of the present invention and a plurality of coloring materials of other colors are combined with each other, an EC element that absorbs all light beams in a visible region to be colored black may be produced.

Examples of the coloring material of any other color that may be used in the EC element of the present invention include the following compounds. Other EC compounds that are colored in oxidized states include: phenazine-based compounds, such as 5,10-dihydro-5,10-dimethylphenazine and 5,10-dihydro-5,10-diethylphenazine; metallocene-based compounds, such as ferrocene, tetra-t-butylferrocene, and titanocene; phenylenediamine-based compounds, such as N,N,N',N'-tetramethyl-p-phenylenediamine; and pyrazoline-based compounds, such as 1-phenyl-2-pyrazoline.

Other compounds that are colored in reduced states include: viologen-based compounds, such as N,N'-diheptyl bipyridinium diperchlorate, N,N'-diheptyl bipyridinium ditetrafluoroborate, N,N'-diheptyl bipyridinium dihexafluorophosphate, N,N'-diethyl bipyridinium diperchlorate, N,N'-diethyl bipyridinium ditetrafluoroborate, N,N'-diethyl bipyridinium dihexafluorophosphate, N,N'-dibenzyl bipyridinium diperchlorate, N,N'-dibenzyl bipyridinium ditetrafluoroborate, N,N'-dibenzyl bipyridinium dihexafluorophosphate, N,N'-diphenyl bipyridinium diperchlorate, N,N'-diphenyl bipyridinium ditetrafluoroborate, and N,N'-diphenyl bipyridinium dihexafluorophosphate; anthraquinone-based compounds, such as 2-ethyl anthraquinone, 2-t-butyl anthraquinone, and octamethyl anthraquinone; ferrocenium salt-based compounds, such as ferrocenium tetrafluoroborate and ferrocenium hexafluorophosphate; and styrylated compounds.

(Substrates 10)

For example, a colorless or colored glass, or a tempered glass is used as each of the substrates 10, in particular, transparent substrates. Alternatively, a colorless or colored transparent resin is used. The term "transparent" in the EC element of the present invention means that a visible light transmittance is 80% or more. Specific examples thereof include polyethylene terephthalate, polyethylene naphthalate, polynorbornene, polyamide, polysulfone, polyethersulfone, polyether ether ketone, polyphenylene sulfide, polycarbonate, polyimide, and polymethyl methacrylate.

(Electrode 11)

As a material for the electrode 11, particularly for the transparent electrode, there may be given, for example: metals or metal oxides, such as an indium tin oxide alloy (ITO), fluorine-doped tin oxide (FTO), tin oxide (NESA), indium zinc oxide (IZO), silver oxide, vanadium oxide, molybdenum oxide, gold, silver, platinum, copper, indium, and chromium; silicon-based materials, such as polycrystalline silicon and amorphous silicon; and carbon materials, such as carbon black, graphite, and glassy carbon. In addition, conductive polymers, such as polyaniline, polypyrrole, polythiophene, polyacetylene, poly(p-phenylene), and a complex of polyethylenedioxythiophene (PEDOT) and polystyrene sulfonate, the conductive polymers each having improved conductivity with doping treatment or the like, are also suitably used.

Further, the electrodes 11 may have porous electrodes. The porous electrodes are each preferably formed of a material having a large surface area, such as a material of a porous shape, rod shape, or wire shape having fine pores on its surface and in itself. As a material for the porous electrode, for example, a metal, a metal oxide, or carbon may be adopted. The material is more preferably a metal oxide, such as titanium oxide, tin oxide, iron oxide, strontium oxide, tungsten oxide, zinc oxide, tantalum oxide, vanadium oxide, indium oxide, nickel oxide, manganese oxide, or cobalt oxide.

(Spacers 13)

The spacers 13 are arranged between the pair of electrodes 11, and provide a space for storing the solution containing the organic compound of the present invention, the solution serving as the EC layer 12. Specifically, for example, polyimide, polytetrafluoroethylene, polyester, a fluorine rubber, or an epoxy resin may be used. The inter-electrode distance of the EC element 14 can be kept by the spacers 13.

The EC element of the present invention may include a liquid injection hole formed by the pair of electrodes 11 and the spacers 13. After the solution containing the organic compound of the present invention has been injected from the liquid injection hole, the injection hole is covered with a sealing member, and is hermetically sealed with an adhesive or the like. Thus, the EC element of the present invention can be obtained. The sealing member also serves to isolate the adhesive and the organic compound of the present invention so that the adhesive and the organic compound may be out of contact with each other. Although the shape of the sealing member is not particularly limited, a tapered shape, such as a wedge shape, is preferred.

A method of injecting the solution containing the organic compound of the present invention is not particularly limited, and for example, the following method may be used: the solution containing the organic compound of the present invention prepared in advance is injected into a gap arranged between the pair of electrodes 11 by a vacuum injection method, an atmospheric injection method, or a meniscus method.

<Application and the Like of EC Element 14>

The quantity of light passing through the EC element 14 of the present invention can be adjusted by driving the EC element, and hence the EC element can be used in, for example, an optical filter, a lens unit, an image pickup apparatus, or a window member.

(Optical Filter)

An optical filter of the present invention includes the EC element 14 of the present invention and an active element connected to the EC element 14. The optical filter of the present invention may include a peripheral device. The active element may be directly connected to the EC element 14, or may be indirectly connected thereto through any other element. Examples of the active element include a TFT element and a MIM element. In the optical filter of the present invention, the active element is configured to drive the EC element 14 to adjust the quantity of light passing through the EC element 14.

The optical filter of the present invention may be used in an image pickup apparatus, such as a camera, and when the optical filter is used in the image pickup apparatus, the optical filter may be arranged in the main body of the image pickup apparatus, or may be arranged in a lens unit thereof. A case in which a neutral density (ND) filter is formed by using the optical filter of the present invention is described below.

The neutral density filter is a filter that achieves black absorption, and requires uniform light absorption in a visible light region. The following suffices for the achievement of the black absorption of the neutral density filter using an EC compound: an EC element in which a plurality of materials having different absorption regions in the visible light region are mixed is produced, and its absorption spectrum in the visible light region is flattened. The absorption spectrum when the EC compounds are mixed is represented by the sum of the absorption spectra of the respective EC compounds. Accordingly, the black absorption of the neutral density filter can be achieved by: selecting a plurality of EC compounds having proper wavelength regions; and adjusting their concentrations.

Examples of the driving of the neutral density filter using the optical filter of the present invention are described below. In general, the neutral density filter reduces the quantity of light to $½^n$ (where n represents a positive integer). When the quantity of light is reduced to ½, the transmittance is reduced from 100% to 50%. When the quantity of light is reduced to ¼, the transmittance is reduced from 100% to 25%. In addition, when the transmittance is reduced to ½, from a relationship of −log (transmittance)=(absorbance), the absorbance change amount is 0.3, and when the transmittance is reduced to ¼, the absorbance change amount is 0.6. For example, in order to set the transmittance to from ½ to ¹⁄₆₄, it is only required that the absorbance change amount be controlled to be from 0 to 1.8 in units of 0.3.

When the EC layer 12 is a solution, the variation in absorbance includes the variation component of a coloring amount resulting from a fluctuation. In order to precisely control the variation in absorbance, an external monitor configured to measure the light quantity may be attached as part of the optical filter.

(Lens Unit and Image Pickup Apparatus)

A lens unit of the present invention includes the optical filter of the present invention and an image pickup optical system having a plurality of lenses. In the lens unit of the present invention, the respective components may be arranged so that light that has passed through the optical filter of the present invention may pass through the image pickup optical system, or the respective components may be arranged so that light that has passed through the image pickup optical system may pass through the optical filter of the present invention.

In addition, an image pickup apparatus of the present invention includes the optical filter of the present invention and an image pickup element configured to receive light that has passed through the optical filter.

Figure 2A:
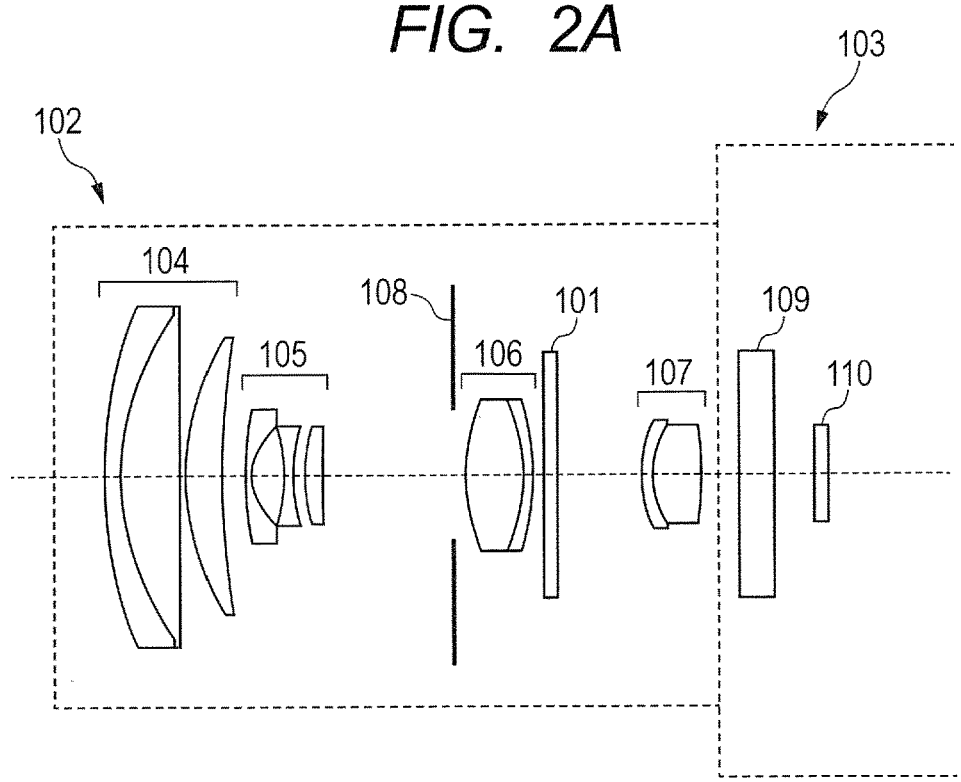
FIG. 2A and FIG. 2B are each a schematic sectional view of an image pickup apparatus of the present invention.
Figure 2B:
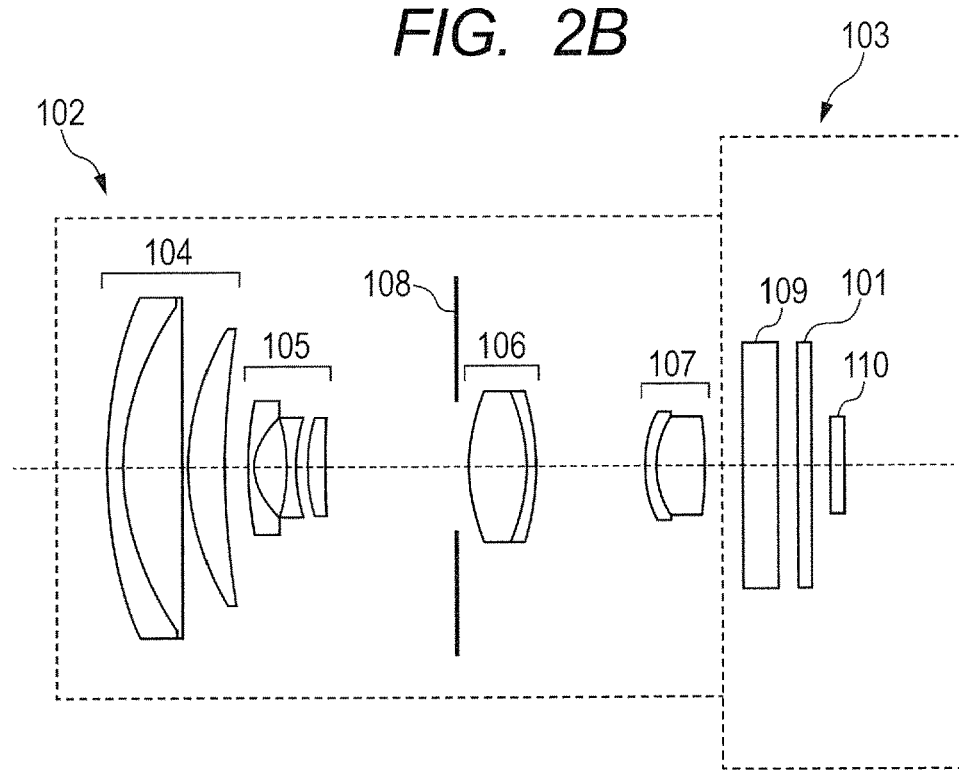

FIG. 2A and FIG. 2B are each a schematic view for illustrating the image pickup apparatus using the optical filter of the present invention. FIG. 2A is an illustration of an image pickup apparatus including a lens unit 102 using an optical filter 101 of the present invention, and FIG. 2B is an illustration of an image pickup apparatus including the optical filter 101 of the present invention. As illustrated in each of FIG. 2A and FIG. 2B, the lens unit 102 is removably connected to an image pickup unit 103 through a mounting member (not shown).

The lens unit 102 is a unit including a plurality of lenses or lens groups. For example, the lens unit 102 illustrated in FIG. 2A is a rear-focus zoom lens configured to perform focusing behind a diaphragm. The lens unit 102 includes, in order from a subject side (left side of the drawing), four lens groups of a first lens group 104 having a positive refractive power, a second lens group 105 having a negative refractive power, a third lens group 106 having a positive refractive power, and a fourth lens group 107 having a positive refractive power. An interval between the second lens group 105 and the third lens group 106 is changed to vary magnification, and a part of lenses of the fourth lens group 107 is moved to perform focusing. For example, the lens unit 102 includes a diaphragm 108 arranged between the second lens group 105 and the third lens group 106, and further includes the optical filter 101 of the present invention arranged between the third lens group 106 and the fourth lens group 107. Those components are arranged so that the light passing through the lens unit 102 may pass through the lens groups 104 to 107, the diaphragm 108, and the optical filter 101 of the present invention, and the quantity of light can be adjusted with the use of the diaphragm 108 and the optical filter 101 of the present invention.

In addition, a configuration of the components of the lens unit 102 may be modified appropriately. For example, the optical filter 101 of the present invention may be arranged in front of the diaphragm 108 (on the subject side thereof), or may be arranged behind the diaphragm 108 (on the image pickup unit 103 side thereof). Alternatively, the optical filter 101 of the present invention may be arranged in front of the first lens group 104, or may be arranged behind the fourth lens group 107. When the optical filter 101 of the present invention is arranged at a position where light converges, there is an advantage in that the area of the optical filter 101 of the present invention can be reduced, for example. In addition, a mode of the lens unit 102 may also be selected appropriately. Instead of the rear-focus zoom lens, the lens unit 102 may also be an inner-focus zoom lens configured to perform focusing in front of the diaphragm, or may be another type of zoom lens configured to perform focusing in another way. In addition, instead of the zoom lens, a special-purpose lens, such as a fisheye lens or a macro lens, may also be selected appropriately.

A glass block 109 included in the image pickup unit 103 is a glass block such as a low-pass filter, a face plate, or a color filter. In addition, the image pickup element 110 is a sensor unit configured to receive light that has passed through the lens unit 102, and a CCD, a CMOS, or the like may be used as the image pickup element 110. In addition, the image pickup element 110 may also be an optical sensor, such as a photodiode, and a device configured to acquire and output information on the intensity or wavelength of light may be used appropriately as the image pickup element 110.

When the optical filter 101 of the present invention is built into the lens unit 102 as illustrated in FIG. 2A, a driving unit may be arranged within the lens unit 102, or may be arranged outside the lens unit 102, for example, within the image pickup unit 103. When the driving unit is arranged outside the lens unit 102, the EC element and the driving unit, which are respectively arranged within and outside the lens unit 102, are connected to each other through wiring, and the driving unit drives and controls the EC element.

As illustrated in FIG. 2B, the image pickup unit 103 may include the optical filter 101 of the present invention. The optical filter 101 of the present invention is arranged at an appropriate position within the image pickup unit 103, and it is only required that the image pickup element 110 be arranged so as to receive the light that has passed through the optical filter 101 of the present invention. In FIG. 2B, for example, the optical filter 101 of the present invention is arranged immediately in front of the image pickup element 110. When the image pickup unit 103 has the optical filter 101 of the present invention built therein, the lens unit 102 itself connected to the image pickup unit does not need to include the optical filter 101 of the present invention, and hence the image pickup apparatus using an existing lens unit and being capable of controlling light can be formed.

The image pickup apparatus described above is applicable to a product having a combination of a function of adjusting a light quantity and an image pickup element. The image pickup apparatus can be used in, for example, a camera, a digital camera, a video camera, or a digital video camera. The image pickup apparatus is also applicable to a product having the image pickup apparatus built therein, such as a mobile phone, a smartphone, a PC, or a tablet computer.

Through the use of the optical filter 101 of the present invention as a light control member, a light quantity to be controlled can be appropriately varied with the use of one filter, and there are advantages in that the number of members can be reduced and that a space can be saved, for example.

(Window Member)

Figure 3A:
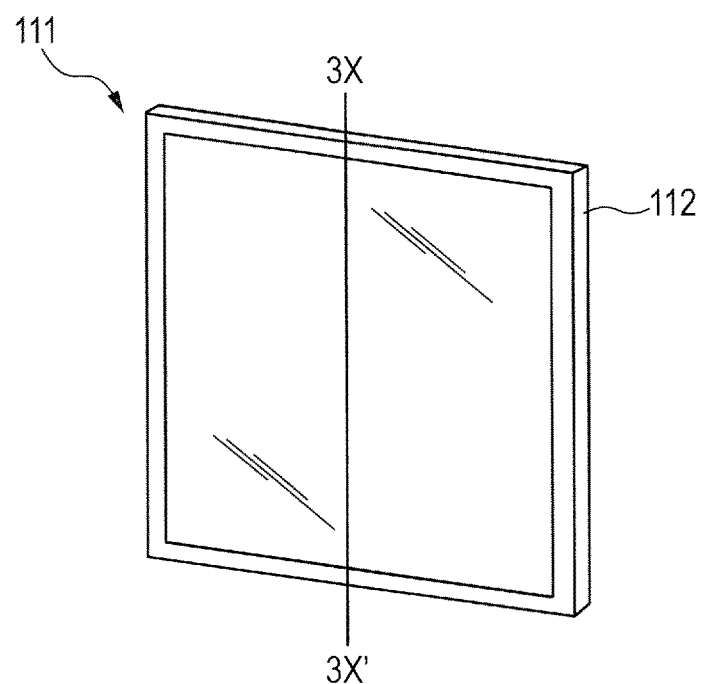
FIG. 3A and FIG. 3B are each a view for illustrating an example of a window member of the present invention.
Figure 3B:
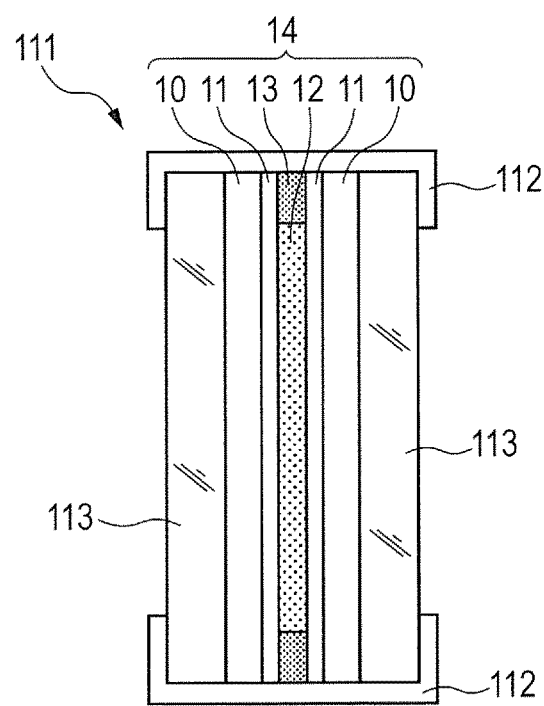

A window member of the present invention includes the EC element 14 of the present invention. The window member of the present invention preferably includes a driving unit for driving the EC element 14. FIG. 3A and FIG. 3B are views for illustrating the window member of the present invention. FIG. 3A is a perspective view and FIG. 3B is a sectional view taken along the line 3X-3X' of FIG. 3A.

As illustrated in FIG. 3A and FIG. 3B, a window member 111 is a light control window, and includes an EC element 14, transparent plates 113 configured to sandwich the element, and a frame 112 configured to surround the entirety to integrate the element and the plates. The driving unit may be integrated in the frame 112, or may be connected to the EC element 14 through a wiring arranged outside the frame 112.

The transparent plates 113 are not particularly limited as long as the plates are made of materials each having a high light transmittance. Considering the use of the window member 111 as a window, it is preferred that the transparent plates 113 be made of glass materials. In FIG. 3B, the EC element 14 is a constituent member independent of the transparent plates 113, but for example, the substrates 10 of the EC element 14 may be regarded as the transparent plates 113.

A material for the frame 112 is not limited, but any member that covers at least a part of the EC element 14 and has a form of being integrated into one frame may be regarded as the frame.

The window member of the present invention serving as the light control window is applicable to, for example, use of adjusting a quantity of sunlight entering a room during the daytime. The window member is applicable to adjust not only the quantity of sunlight but also a heat quantity, and hence can be used to control brightness and temperature of the room. In addition, the window member is also applicable to use as a shutter to prevent an indoor view from being seen from the outside of the room. The light control window described above is applicable not only to a glass window for a construction, but also to a window of a vehicle, such as an automobile, a train, an airplane, or a ship, and to a filter of a display surface of a clock, a watch, or a mobile phone.

Now, description is made of Examples, but the present invention is not limited to the following Examples.

Example 1 (Synthesis of Exemplified Compound A-1)

(1) Synthesis of Intermediate 1

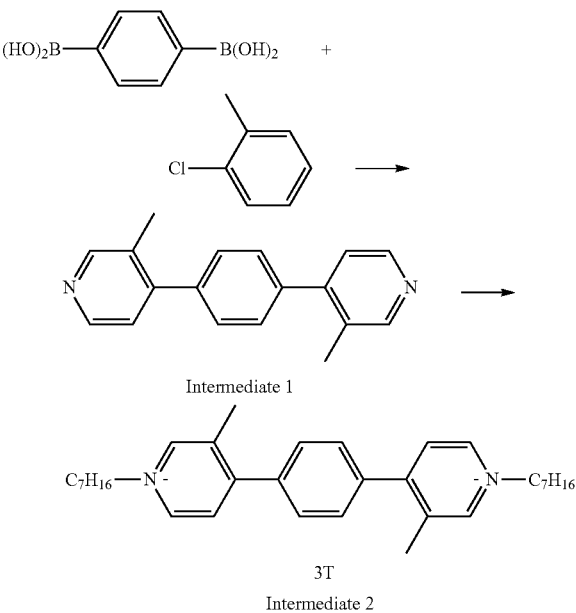

First, Intermediate 1 was synthesized. 1,4-Phenylenediboronic acid (0.20 g, 1.2 mmol), 4-chloro-3-methylpyridine (0.46 g, 3.6 mmol), tetrakis(triphenylphosphine)palladium (0.07 g, 0.06 mmol), tripotassium phosphate (0.77 g, 3.6 mmol), dioxane (30 ml), and water (10 ml) were loaded into a reaction vessel, and were stirred in a stream of nitrogen for 8 hours under reflux. After the completion of the reaction, the reaction liquid was concentrated and then extracted with chloroform. The organic layer was washed with water and dried over magnesium sulfate, followed by evaporation to dryness under reduced pressure. The resultant was purified by silica gel column chromatography (eluent: chloroform/hexane=4/1) to provide 0.1 g (yield: 32%) of Intermediate 1. The structure of Intermediate 1 was identified by $^1$H NMR measurement. $^1$H NMR (DMSO-d6, 500 MHz) σ (ppm): 8.51 (s, 2H), 8.45 (t, 2H), 7.52 (m, 4H), 7.30 (m, 2H), 2.29 (s, 6H).

(2) Synthesis of Intermediate 2

Next, Intermediate 2 was synthesized by using Intermediate 1. Intermediate 1 (0.100 g, 0.38 mmol), 1-iodoheptane (0.347 g, 1.53 mmol), and 10 ml of N,N-dimethylformamide were loaded into a reaction vessel, and were stirred in a stream of nitrogen for 10 hours under reflux. After the completion of the reaction, the reaction liquid was dropped into ethyl acetate, and the resultant precipitate was washed with ethyl acetate to provide 0.219 g (yield: 80%) of Intermediate 2. The structure of Intermediate 2 was identified by 1H NMR measurement.

1H NMR (DMSO-d6, 500 MHz) σ (ppm): 9.15 (s, 2H), 9.02 (d, 2H), 8.11 (d, 2H), 7.80 (m, 4H), 4.59 (t, 4H), 1.95 (t, 4H), 2.54 (s, 6H), 1.30 (m, 16H), 0.85 (t, 6H).

(3) Synthesis of Exemplified Compound A-1

Next, Exemplified Compound A-1 was synthesized by using Intermediate 2. First, Intermediate 2 (0.219 g, 0.31 mmol) was dissolved in water. An aqueous solution of ammonium hexafluorophosphate was dropped into the solution, and the mixture was stirred at room temperature for 3 hours. The precipitated crystal was filtered, and was sequentially washed with isopropyl alcohol and diethyl ether to provide 0.207 g (yield: 90%) of Exemplified Compound A-1. The structure of Exemplified Compound A-1 was identified by 1H NMR measurement.

1H NMR (DMSO-d6, 500 MHz) σ (ppm): 9.15 (s, 2H), 9.00 (m, 2H), 8.12 (m, 2H), 7.80 (m, 4H), 4.58 (t, 4H), 1.95 (t, 4H), 2.54 (s, 6H), 1.30 (m, 16H), 0.86 (t, 6H).

Example 2

The EC element 14 illustrated in FIG. 1 was produced by using Exemplified Compound A-1, and its characteristic evaluation was performed. Tetrabutylammonium perchlorate serving as an electrolyte was dissolved at a concentration of 0.1 M in propylene carbonate. Next, Exemplified Compound A-1 was dissolved at a concentration of 40.0 mM in the solution. Thus, an EC medium forming the EC layer 12 was obtained.

Glass substrates with transparent conductive films (transparent electrode films) were used as the substrates 10 and electrodes 11 of the EC element 14. Insulating layers (SiO$_2$) were formed in the four end portions of the pair of glass substrates with the transparent conductive films (ITO) PET films (MELINEX (trademark) S, thickness: 125 μm, manufactured by Teijin DuPont Films) serving as the spacers 13 configured to specify a substrate interval are arranged between the pair of glass substrates with the transparent electrode films. After that, the glass substrates and the PET films were bonded to each other with an epoxy-based adhesive while an injection hole for EC medium injection was left, followed by sealing. Thus, an empty cell with the injection hole was produced.

Next, the EC medium containing Exemplified Compound A-1 was injected from the injection hole by a vacuum injection method, and then the injection hole was sealed with an epoxy-based adhesive. Thus, the EC element was obtained.

Figure 4:
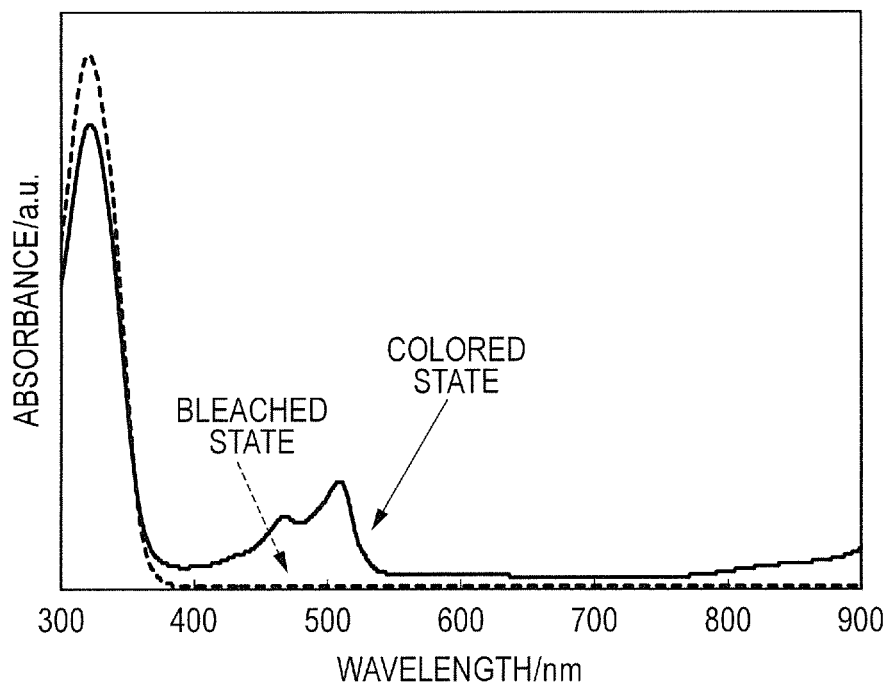
FIG. 4 is the ultraviolet-visible absorption spectra of an EC element of Example 2 in its colored state and bleached state.

The application of a voltage of 1.5 V to the EC element of this example caused the EC element to show coloring derived from a reduced species of Exemplified Compound A-1 in the EC element. Further, the application of a voltage of −0.5 V led to the bleaching of the EC element. That is, it was revealed that the EC element of this example was able to reversibly change its colored state and bleached state, and hence had an EC property. The ultraviolet-visible absorption spectra of the EC element of this example in the colored state and the bleached state are shown in FIG. 4. Exemplified Compound A-1 has a local maximum absorption wavelength at 570 nm in the reduced state.

Comparative Example 1

An EC element was produced by using Comparative Compound 1 having a pentacyclic structure represented by the following structure, and its absorption wavelength in a reduced state was measured.

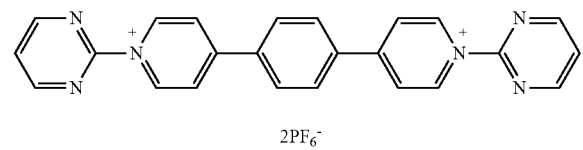

Comparative Compound 1

Figure 5:
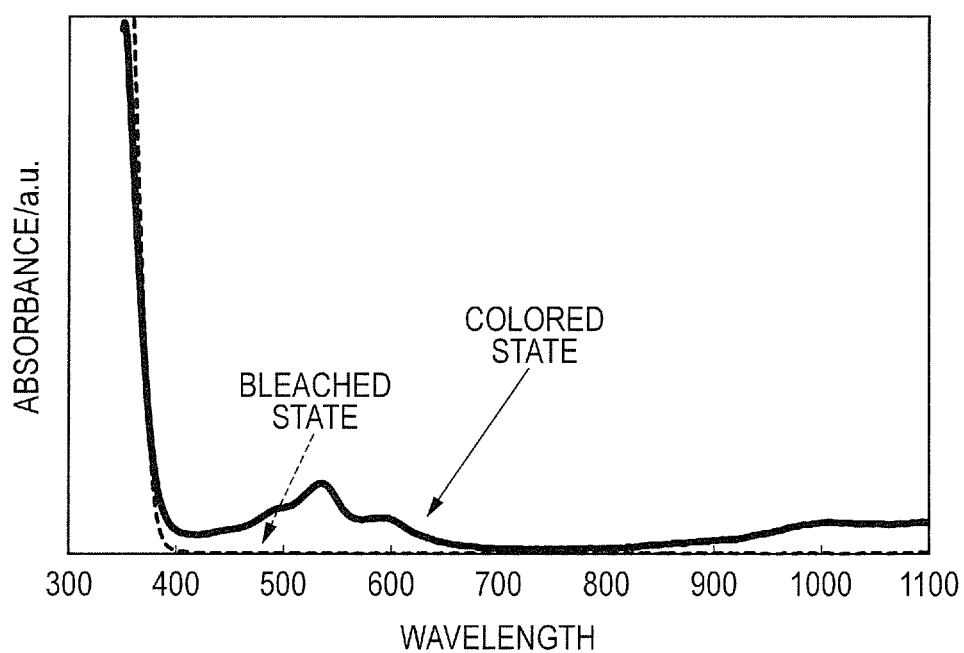
FIG. 5 is the ultraviolet-visible absorption spectra of an EC element of Comparative Example 1 in its colored state and bleached state.

An evaluation was performed by the same method as that of Example 2 except that Comparative Compound 1 was used instead of Exemplified Compound A-1. The ultraviolet-visible absorption spectra of the EC element of this comparative example in its colored state and bleached state are shown in FIG. 5. Comparative Compound 1 has a local maximum absorption wavelength at 550 nm in the reduced state. It was found from the foregoing that Comparative Compound 1 had pyrimidyl groups at both of its terminals, and hence the absorption wavelength in the reduced state shifted to a red light region as compared to an absorption wavelength expected from a typical pentacyclic compound, but the compound had the absorption wavelength in a wavelength region shorter than that of Exemplified Compound A-1.

As described above, according to the organic compound of the present invention, there can be provided a material whose absorption wavelength in a reduced state can be lengthened as compared to those of a compound having a tricyclic structure and a compound having a pentacyclic structure, the compounds each being free of any twisted structure, by introducing a twisted structure.

According to the present invention, there can be provided such an organic compound that its absorption wavelength in a reduced state can be lengthened while its transparency at the time of bleaching is maintained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-028821, filed Feb. 20, 2017, which is hereby incorporated by reference herein in its entirety.

What is claimed is:

1. An organic compound, which is represented by the general formula (1):

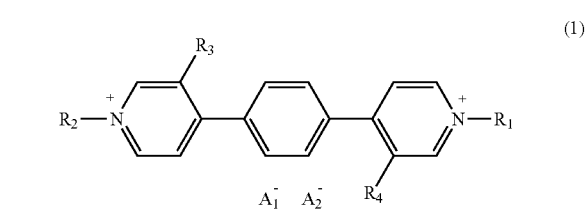

in the general formula (1), $R_1$ and $R_2$ are each independently selected from the group consisting of an alkyl group having 1 or more and 20 or less carbon atoms, an aryl group, an aralkyl group, and a heteroaryl group, and the alkyl group, the aryl group, the aralkyl group, and the heteroaryl group may each have a substituent; $R_3$ and $R_4$ are each independently selected from the group consisting of an alkyl group having 1 or more and 10 or less carbon atoms, and an alkoxy group having 1 or more and 10 or less carbon atoms; and $A_1^-$ and $A_2^-$ each independently represent a monovalent anion.

2. An organic compound according to claim 1, wherein the organic compound has a local maximum absorption wavelength in a range of from 570 nm or more to 800 nm or less in a reduced state.

3. An organic compound according to claim 1, wherein the substituents that the $R_1$ and the $R_2$ may have are each independently selected from the group consisting of a halogen atom, an alkyl group having 1 or more and 4 or less carbon atoms, an alkoxy group having 1 or more and 4 or less carbon atoms, an aryl group, an aralkyl group, and a heteroaryl group.

4. An organic compound according to claim 3, wherein the $R_1$ and the $R_2$ are each independently selected from the group consisting of the aryl group, the aralkyl group, and the heteroaryl group, and the $R_1$ and the $R_2$ have the substituents.

5. An organic compound according to claim 1, wherein the $A_1^-$ and the $A_2^-$ are identical to each other.

6. An organic compound according to claim 1, wherein the $R_3$ and the $R_4$ are identical to each other.

7. An electrochromic element, comprising:
a pair of electrodes; and
an electrochromic layer arranged between the pair of electrodes,
wherein the electrochromic layer contains the organic compound of claim 1.

8. An electrochromic element according to claim 7, wherein the electrochromic layer further contains another kind of organic compound different from the organic compound represented by the general formula (1).

9. An electrochromic element according to claim 8, wherein the another kind of organic compound is one of a phenazine-based compound, a metallocene-based compound, a phenylenediamine-based compound, and a pyrazoline-based compound.

10. An electrochromic element according to claim 7, wherein the electrochromic layer is a liquid containing an electrolyte.

11. An optical filter, comprising:
the electrochromic element of claim 7; and
an active element connected to the electrochromic element.

12. An optical filter according to claim 11, wherein the active element is configured to drive the electrochromic element to adjust a quantity of light passing through the electrochromic element.

13. A lens unit, comprising:
the optical filter of claim 11; and
an image pickup optical system having a plurality of lenses.

14. An image pickup apparatus, comprising:
the optical filter of claim 11; and
an image pickup element configured to receive light passing through the optical filter.

15. A window member, comprising the electrochromic element of claim 7.

* * * * *